(12) United States Patent
Matsuo

(10) Patent No.: US 11,247,203 B2
(45) Date of Patent: Feb. 15, 2022

(54) PIPETTE TIP, LIQUID DELIVERY METHOD AND LIQUID DELIVERY SYSTEM

(71) Applicant: Konica Minolta, Inc., Tokyo (JP)

(72) Inventor: Masataka Matsuo, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 330 days.

(21) Appl. No.: 16/319,983

(22) PCT Filed: Jul. 19, 2017

(86) PCT No.: PCT/JP2017/026053
§ 371 (c)(1),
(2) Date: Jan. 24, 2019

(87) PCT Pub. No.: WO2018/021103
PCT Pub. Date: Feb. 1, 2018

(65) Prior Publication Data
US 2019/0247843 A1   Aug. 15, 2019

(30) Foreign Application Priority Data
Jul. 26, 2016   (JP) .............................. JP2016-146387

(51) Int. Cl.
*B01L 3/02* (2006.01)
*C12M 1/00* (2006.01)
(Continued)

(52) U.S. Cl.
CPC ............. *B01L 3/021* (2013.01); *B01L 3/0275* (2013.01); *B01L 3/0286* (2013.01); *B01L 3/502* (2013.01);
(Continued)

(58) Field of Classification Search
None
See application file for complete search history.

(56) References Cited

U.S. PATENT DOCUMENTS 4,917,274 A    4/1990  Asa et al.
2005/0255005 A1*  11/2005  Motadel ................ B01L 3/0275
                                                    422/400
(Continued)

FOREIGN PATENT DOCUMENTS

EP    1110609 A2    6/2001
EP    1839752 A2    10/2007
(Continued)

OTHER PUBLICATIONS

Saito etal, Machine Translation of description for JP2008020376A (Year: 2008).*

(Continued)

*Primary Examiner* — Matthew D Krcha
*Assistant Examiner* — Brittany I Fisher
(74) *Attorney, Agent, or Firm* — Lucas & Mercanti, LLP

(57) ABSTRACT

This pipette tip includes: a first part having an outer diameter which increases gradually from a distal end side toward a proximal end side; a second part in which a taper angle of an outer surface of the second part is smaller than a taper angle of an outer surface of the first part; a third part in which a taper angle of an outer surface of the third part is larger than the taper angle of the outer surface of the first part; and a fourth in which a taper angle of an outer surface of the fourth part is smaller than the taper angle of the outer surface of the third part.

13 Claims, 8 Drawing Sheets

(51) Int. Cl.
    *G01N 1/00*       (2006.01)
    *G01N 35/10*     (2006.01)
    *B01L 3/00*       (2006.01)
    *G01N 21/64*     (2006.01)

(52) U.S. Cl.
    CPC ............... *C12M 1/00* (2013.01); *G01N 1/00* (2013.01); *G01N 35/10* (2013.01); *B01L 2200/087* (2013.01); *B01L 2300/044* (2013.01); *B01L 2300/0858* (2013.01); *B01L 2400/0406* (2013.01); *G01N 21/64* (2013.01)

(56) References Cited

U.S. PATENT DOCUMENTS

| | | | |
|---|---|---|---|
| 2007/0231215 A1 | 10/2007 | Mototsu et al. | |
| 2010/0028985 A1 | 2/2010 | Hanafusa et al. | |
| 2011/0183433 A1* | 7/2011 | Motadel | B01L 3/0279 436/180 |
| 2012/0115238 A1* | 5/2012 | Akashi | B01L 3/502 436/94 |
| 2016/0051979 A1* | 2/2016 | Herbst | B01L 3/0279 73/864.01 |
| 2016/0245803 A1* | 8/2016 | Murayama | G01N 21/77 |

FOREIGN PATENT DOCUMENTS

| | | |
|---|---|---|
| JP | H08-266913 A | 10/1996 |
| JP | 2007271427 A | 10/2007 |
| JP | 2008020376 A | 1/2008 |
| JP | 2013185967 A | 9/2013 |
| JP | 2016080558 A | 5/2016 |
| WO | 2006104213 A1 | 10/2006 |

OTHER PUBLICATIONS

International Search Report dated Oct. 17, 2017 for PCT/JP2017/026053 and English translation.
EPO, Office Action for the corresponding European Patent Application No. 17834111.1, dated May 28, 2020.
EPO, Extended European Search Report for the corresponding European Patent Application No. 17834111.1, dated Jun. 26, 2019 (10 pages).
International Preliminary Report on Patentability dated Feb. 7, 2019 from corresponding International Application PCT/JP2017/026053.
Office Action for the corresponding Japanese Patent Application No. 2018-529799 dated Aug. 25, 2020 and translation.
JPO, Office Action for the corresponding Japanese Patent Application No. 2018-529799, dated Nov. 17, 2020, with English translation.

* cited by examiner

PIPETTE TIP, LIQUID DELIVERY METHOD AND LIQUID DELIVERY SYSTEM

CROSS REFERENCE TO RELATED APPLICATION

This Application is a 371 of PCT/JP2017/026053 filed on Jul. 19, 2017 which, in turn, claimed the priority of Japanese Patent Application No. 2016-146387 filed on Jul. 26, 2016, both applications are incorporated herein by reference.

TECHNICAL FIELD

The present invention relates to a liquid delivery method and a liquid delivery system, for injecting a liquid into a channel of a channel chip and sucking a liquid from the channel of the channel chip with use of a pipette tip, and relates to a pipette tip that can be used in these.

BACKGROUND ART

Biochemical reactions such as antigen-antibody reactions are used in biochemical examinations. For example, in a fluorescent immunoassay (hereinafter also referred to as "FIA"), a substance to be detected (antigen) is reacted with a labeling substance containing a fluorescent substance. Thereafter, fluorescence emitted by the fluorescent substance is detected by irradiating, with excitation light, the substance to be detected that has been labeled with the labeling substance. Then, from an intensity of the detected fluorescence and the like, an amount of the substance to be detected is specified. Among such FIAs, as a method capable of detecting a substance to be detected with particularly high sensitivity, surface plasmon-field enhanced fluorescence spectroscopy (hereinafter also referred to as "SPFS") is known.

In SPFS, a first capturing body (e.g., a primary antibody) capable of specifically binding to a substance to be detected is fixed on a metal film to form a reaction field for capturing the substance to be detected. Usually, the reaction field is formed in a fine channel. Then, a sample liquid (specimen) containing the substance to be detected is injected into this channel, thereby binding the substance to be detected to the first capturing body (primary reaction). Subsequently, a fluorescent labeling liquid containing a second capturing body (e.g., a secondary antibody) labeled with a fluorescent substance is injected into the channel, thereby further binding the second capturing body to the substance to be detected bound to the primary antibody (secondary reaction). That is, the substance to be detected is indirectly labeled with the fluorescent substance. When the metal film is irradiated with excitation light in this state, the fluorescent substance is excited by the electric field enhanced by surface plasmon resonance (hereinafter also referred to as "SPR") to emit fluorescence. Then, the substance to be detected can be detected by detecting the fluorescence emitted by the fluorescent substance.

PTL 1 discloses a biochemical examination apparatus that detects a substance to be detected with use of SPFS. This biochemical examination apparatus includes: an inspection chip having a channel formed with a reaction field inside; a reagent chip having a plurality of vessels each containing different types of reagents; a liquid delivery mechanism to move a liquid between the reagent chip and the inspection chip; a conveyance mechanism to move the inspection chip; a measurement unit to irradiate the inspection chip with excitation light and to detect fluorescence from the inspection chip, and the like.

FIG. 1 is a schematic view showing reagent chip 10 and inspection chip 20 in the biochemical examination apparatus described in PTL 1. As shown in FIG. 1, reagent chip 10 includes: cleaning liquid vessel 11 containing a cleaning liquid; specimen vessel 12 containing a specimen; diluent vessel 13 containing a diluent; sample liquid vessel 14 containing a sample liquid obtained by diluting the specimen with the diluent; and fluorescent labeling liquid vessel 15 containing a fluorescent labeling liquid. Further, reagent chip 10 is attached with pipette tip 16. Pipette tip 16 is attached to the liquid delivery mechanism to be used. Inspection chip 20 has channel 21 and pipette tip insertion part (insertion hole) 22 connected to one end of channel 21. An opening of pipette tip insertion part 22 is closed with seal (insertion hole hermetic seal) 23. In the biochemical examination apparatus described in PTL 1, as shown in FIG. 1, pipette tip 16 attached to the liquid delivery mechanism is inserted into any vessel of reagent chip 10 to suck a reagent into pipette tip 16, and then pipette tip 16 is inserted into pipette tip insertion part 22 of inspection chip 20 to inject the reagent into channel 21. While a through hole is formed in seal 23 when pipette tip 16 is initially inserted into pipette tip insertion part 22, this through hole is closed with pipette tip 16 in a state where pipette tip 16 is inserted into pipette tip insertion part 22. Therefore, injecting the liquid in pipette tip 16 into pipette tip insertion part 22 increases pressure inside pipette tip insertion part 22, and causes the liquid to be also injected into channel 21. Similarly, sucking the liquid in pipette tip insertion part 22 into pipette tip 16 lowers pressure in pipette tip insertion part 22, and causes the liquid in channel 21 to be also sucked into pipette tip 16.

In the biochemical examination apparatus described in PTL 1, there is used pipette tip 16 with an outer diameter gradually increasing from a distal end to a proximal end except for the vicinity of the proximal end. In the vicinity of the proximal end, the outer diameter of pipette tip 16 is constant. An inner diameter of pipette tip 16 gradually increases from the distal end toward the proximal end, from the distal end to the proximal end. A taper angle of an inclined surface of an outer surface of pipette tip 16 is constant, and a taper angle of an inclined surface on an inner surface is also constant.

In the biochemical examination apparatus described in PTL 1, an opening of pipette tip insertion part 22 of inspection chip 20 is closed with seal 23, but whether or not an opening of each vessel of reagent chip 10 is closed with a seal is not particularly described. On the other hand, such sealing of an opening of a vessel containing a reagent with a seal has been done since before. For example, PTL 2 discloses a reaction vessel to detect SNP in which openings of a reagent container and a mineral oil container are closed with a film, and a reaction vessel processing apparatus using the reaction vessel. FIG. 2 is a schematic view showing the reaction vessel described in PTL 2. As shown in FIG. 2, the reaction vessel has sample injection part 30, reagent container 31, mineral oil container 32, and reaction part 33, and openings of reagent container 31 and mineral oil container 32 are closed with film 34. In using a liquid in reagent container 31 or mineral oil container 32, the liquid is sucked into pipette tip 35 by pipette tip 35 pierced into film 34.

In the reaction vessel processing apparatus described in PTL 2, there is used pipette tip 35 with an outer diameter gradually increasing from a distal end to a proximal end except for the vicinity of the proximal end. In the vicinity of the proximal end, the outer diameter of pipette tip 35 is constant. A taper angle of an inclined surface of an outer surface of pipette tip 35 is constant.

CITATION LIST

Patent Literatures

PTL 1: Japanese Patent Application Laid-Open No. 2013-185967
PTL 2: WO 2006/104213

SUMMARY OF INVENTION

Technical Problem

Also in the biochemical examination apparatus described in PTL 1, it is conceivable to seal an opening of each vessel of reagent chip 10 with a seal, as described in PTL 2. In this case, as reagent chip 10, there is used a vessel that has an opening closed with a first film and contains a liquid inside, while as inspection chip 20, there is used a channel chip that includes a channel and a pipette tip insertion part connected to one end of the channel and having its opening closed with a second film. Further, the pipette tip is attached to a pipette nozzle of a pipette (liquid delivery mechanism), to be used.

Then, when it is desired to inject the liquid in the vessel into the channel of the channel chip, the pipette tip is pierced into the first film of the vessel to suck the liquid contained in the vessel into the pipette tip, and then the pipette tip is pierced into the second film of the channel chip to inject the liquid held in the pipette tip into the channel via the pipette tip insertion part. Further, when it is desired to remove the liquid in the channel of the channel chip, the pipette tip is pierced into the second film of the channel chip to suck the liquid in the channel into the pipette tip via the pipette tip insertion part, and then the pipette tip is pierced into the first film of a used vessel or an empty vessel (used as a waste liquid container) to discharge the liquid held in the pipette tip into the vessel. After performing these steps, through holes are formed in the first film of the vessel and the second film of the channel chip by piercing the pipette tip. After this, the vessel containing the waste liquid is discarded.

As described above, in a case of using the vessel with the opening closed with the first film, the channel chip having the channel and the pipette tip insertion part with the opening closed with the second film, and the pipette tip, it is necessary to satisfy the following requirement (1), and it is further preferable to satisfy the following requirements (2) and (3).

(1) When the pipette tip is inserted into the pipette tip insertion part of the channel chip, it is necessary that an outer surface of the pipette tip and the second film come into close contact with each other without a gap, and the second film can function as a pressure partition wall that separates pressure inside the pipette tip insertion part from external pressure. If the second film cannot function as the pressure partition wall, it is impossible to properly perform injection of liquid into the channel of the channel chip and suction of liquid from the channel. In order for the second film to function as the pressure partition wall, an outer diameter of a portion of the pipette tip corresponding to the second film needs to be larger than a diameter of a through hole of the second film when the through hole is formed in the second film by insertion of the pipette tip.

(2) It is preferable that a diameter of the through hole formed in the first film of the vessel in order to suck a liquid in the vessel into the pipette tip is as small as possible. Reducing the diameter of the through hole formed in the first film makes it difficult for a reagent remaining in the vessel, waste liquid subsequently injected into the vessel, or the like to spill out of the vessel. Making it difficult for a liquid in the vessel to spill out of the vessel in this way is also preferable from the viewpoint of preventing environmental pollution and biohazard.

(3) A size of the pipette tip and the pipette nozzle to be attached with the pipette tip is preferably as small as possible. Reducing the size of the pipette tip and the pipette nozzle makes it possible to realize downsizing of the system (apparatus).

Accordingly, an object of the present invention is to provide a pipette tip to be used in combination with a vessel having an opening closed with a first film, and with a channel chip having a channel and a pipette tip insertion part with an opening closed with a second film. The pipette tip satisfies the following three requirements: (1) properly performing injection of a liquid into the channel of the channel chip and suction of a liquid from the channel; (2) reducing a size of a through hole formed in the first film of the vessel; and (3) reducing a size of the pipette tip and the pipette nozzle. Further, another object of the present invention is to provide a liquid delivery method and a liquid delivery system using this pipette tip.

Solution to Problem

A pipette tip according to an embodiment of the present invention is a pipette chip to be attached to a pipette nozzle and used in a liquid delivery system performing: a first step of sucking a liquid contained in a vessel into the pipette tip in a state where the pipette tip is inserted through a first film into the vessel of which opening is closed with the first film; a second step of injecting a liquid retained in the pipette tip into a channel in a state where the pipette tip is inserted through a second film into a pipette tip insertion part of a channel chip having the channel and the pipette tip insertion part, the pipette tip insertion part being connected to one end of the channel and having an opening closed with the second film; and a third step of sucking a liquid in the channel into the pipette tip in a state where the pipette tip is inserted through the second film into the pipette tip insertion part of the channel chip, in which A>B is satisfied where A is a length along an axial direction of the pipette tip from a distal end of the pipette tip to the first film when the pipette tip is inserted deepest into the vessel in the first step, and B is a length along an axial direction of the pipette tip from a distal end of the pipette tip to the second film when the pipette tip is inserted deepest into the pipette tip insertion part in the second step and the third step, the pipette tip including: a first part that includes a distal end of the pipette tip and has an outer diameter gradually increasing from a distal end side toward a proximal end side; a second part that is arranged adjacent to the first part on a proximal end side, has an outer diameter being unchanged or gradually increasing from a distal end side toward a proximal end side, and has a smaller taper angle of an outer surface than a taper angle of an outer surface of the first part; a third part that is arranged adjacent to the second part on a proximal end side, has an outer diameter gradually increasing from a distal end side toward a proximal end side, and has a larger taper angle of an outer surface than a taper angle of an outer surface of the first part; and a fourth part that is arranged adjacent to the third part on a proximal end side, has an outer diameter being unchanged or gradually increasing from a distal end side toward a proximal end side, and has a smaller taper angle of an outer surface than a taper angle of an outer surface of the third part.

A liquid delivery method according to an embodiment of the present invention includes: a first step of sucking a liquid contained in a vessel into a pipette tip in a state where the pipette tip is inserted through a first film into the vessel of which opening is closed with the first film; a second step of injecting a liquid retained in the pipette tip into a channel in a state where the pipette tip is inserted through a second film into a pipette tip insertion part of a channel chip having the channel and the pipette tip insertion part, the pipette tip insertion part being connected to one end of the channel and having an opening closed with the second film; and a third step of sucking a liquid in the channel into the pipette tip in a state where the pipette tip is inserted through the second film into the pipette tip insertion part of the channel chip, in which A>B is satisfied where A is a length along an axial direction of the pipette tip from a distal end of the pipette tip to the first film when the pipette tip is inserted deepest into the vessel in the first step, and B is a length along an axial direction of the pipette tip from a distal end of the pipette tip to the second film when the pipette tip is inserted deepest into the pipette tip insertion part in the second step and the third step, the pipette tip including: a first part that includes a distal end of the pipette tip and has an outer diameter gradually increasing from a distal end side toward a proximal end side; a second part that is arranged adjacent to the first part on a proximal end side, has an outer diameter being unchanged or gradually increasing from a distal end side toward a proximal end side, and has a smaller taper angle of an outer surface than a taper angle of an outer surface of the first part; a third part that is arranged adjacent to the second part on a proximal end side, has an outer diameter gradually increasing from a distal end side toward a proximal end side, and has a larger taper angle of an outer surface than a taper angle of an outer surface of the first part; and a fourth part that is arranged adjacent to the third part on a proximal end side, has an outer diameter being unchanged or gradually increasing from a distal end side toward a proximal end side, and has a smaller taper angle of an outer surface than a taper angle of an outer surface of the third part.

A liquid delivery system according to an embodiment of the present invention includes: a vessel that has an opening closed with a first film and contains a liquid inside; a channel chip that has a channel and a pipette tip insertion part, the pipette tip insertion part being connected to one end of the channel and having an opening closed with a second film; and a pipette that has a pipette nozzle and a pipette tip attached to the pipette nozzle, the liquid delivery system performing: a first step of sucking a liquid contained in the vessel into the pipette tip in a state where the pipette tip is inserted through the first film into the vessel; a second step of injecting a liquid retained in the pipette tip into the channel in a state where the pipette tip is inserted through the second film into the pipette tip insertion part of the channel chip; and a third step of sucking a liquid in the channel into the pipette tip in a state where the pipette tip is inserted through the second film into the pipette tip insertion part of the channel chip, in which A>B is satisfied where A is a length along an axial direction of the pipette tip from a distal end of the pipette tip to the first film when the pipette tip is inserted deepest into the vessel in the first step, and B is a length along an axial direction of the pipette tip from a distal end of the pipette tip to the second film when the pipette tip is inserted deepest into the pipette tip insertion part in the second step and the third step, the pipette tip including: a first part that includes a distal end of the pipette tip and has an outer diameter gradually increasing from a distal end side toward a proximal end side; a second part that is arranged adjacent to the first part on a proximal end side, has an outer diameter being unchanged or gradually increasing from a distal end side toward a proximal end side, and has a smaller taper angle of an outer surface than a taper angle of an outer surface of the first part; a third part that is arranged adjacent to the second part on a proximal end side, has an outer diameter gradually increasing from a distal end side toward a proximal end side, and has a larger taper angle of an outer surface than a taper angle of an outer surface of the first part; and a fourth part that is arranged adjacent to the third part on a proximal end side, has an outer diameter being unchanged or gradually increasing from a distal end side toward a proximal end side, and has a smaller taper angle of an outer surface than a taper angle of an outer surface of the third part.

Advantageous Effects of Invention

According to the present invention, it is possible to satisfy three requirements of: (1) properly performing injection of a liquid into the channel of the channel chip and suction of a liquid from the channel; (2) reducing a size of a through hole formed in the first film of the vessel; and (3) reducing a size of the pipette tip and the pipette nozzle

DESCRIPTION OF EMBODIMENTS

Hereinafter, an embodiment of the present invention will be described in detail with reference to the drawings. It should be noted that, in the following description, as an example of a pipette tip, a liquid delivery method, and a liquid delivery system according to the present invention, a description is given to a pipette tip, a liquid delivery method, and a liquid delivery system to be applied to a system that detects a substance to be detected by SPFS (e.g., see, PTL 1). However, the pipette tip, the liquid delivery method, and the liquid delivery system according to the present invention are not limited to these.

Figure 1:
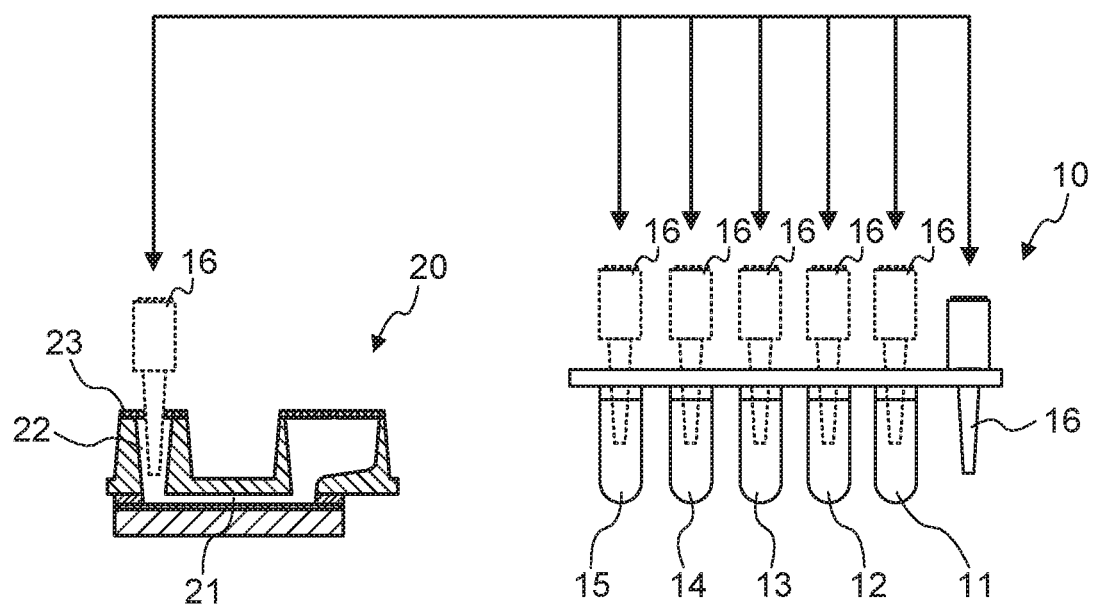
FIG. 1 is a schematic view showing a reagent chip and an inspection chip in a biochemical examination apparatus described in PTL 1.
Figure 2:
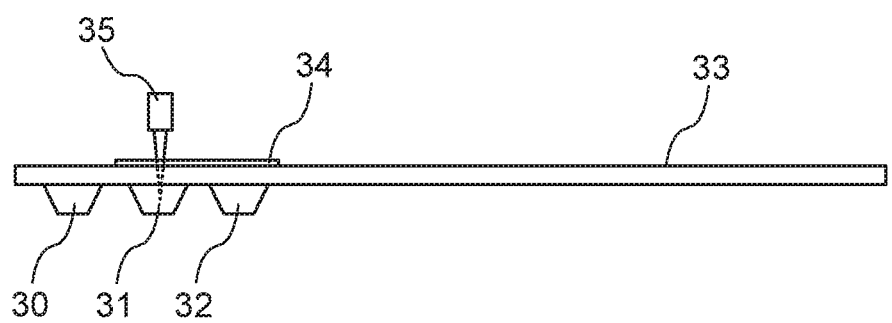
FIG. 2 is a schematic view showing a reaction vessel described in PTL 2.
Figure 3:
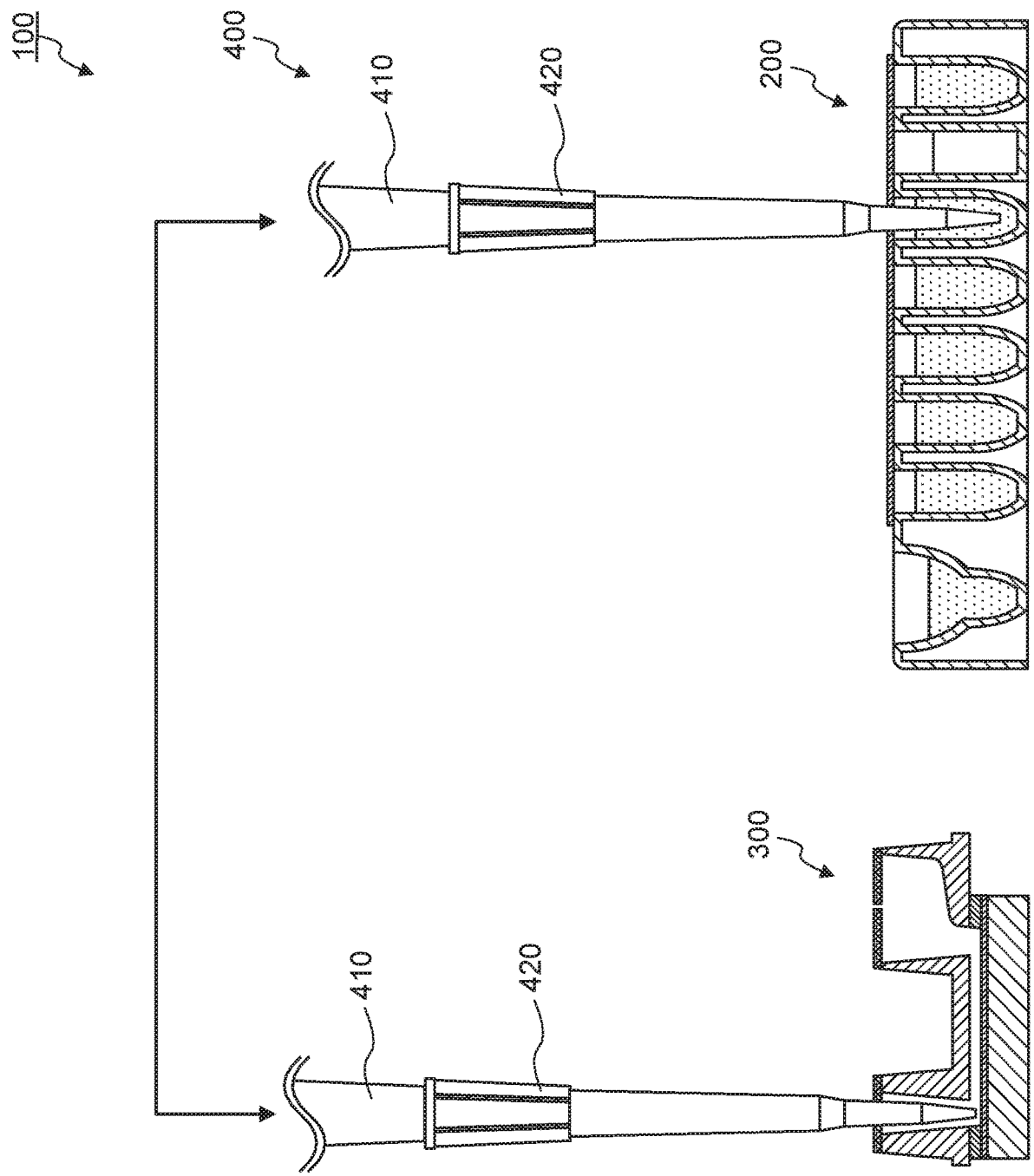
FIG. 3 is a schematic view showing a configuration of a liquid delivery system according to an embodiment of the present invention.

FIG. 3 is a schematic view showing a configuration of liquid delivery system 100 according to an embodiment of the present invention. As shown in FIG. 3, liquid delivery system 100 includes reagent chip 200, channel chip 300, and pipette 400.

(Reagent Chip)

Figure 4A:
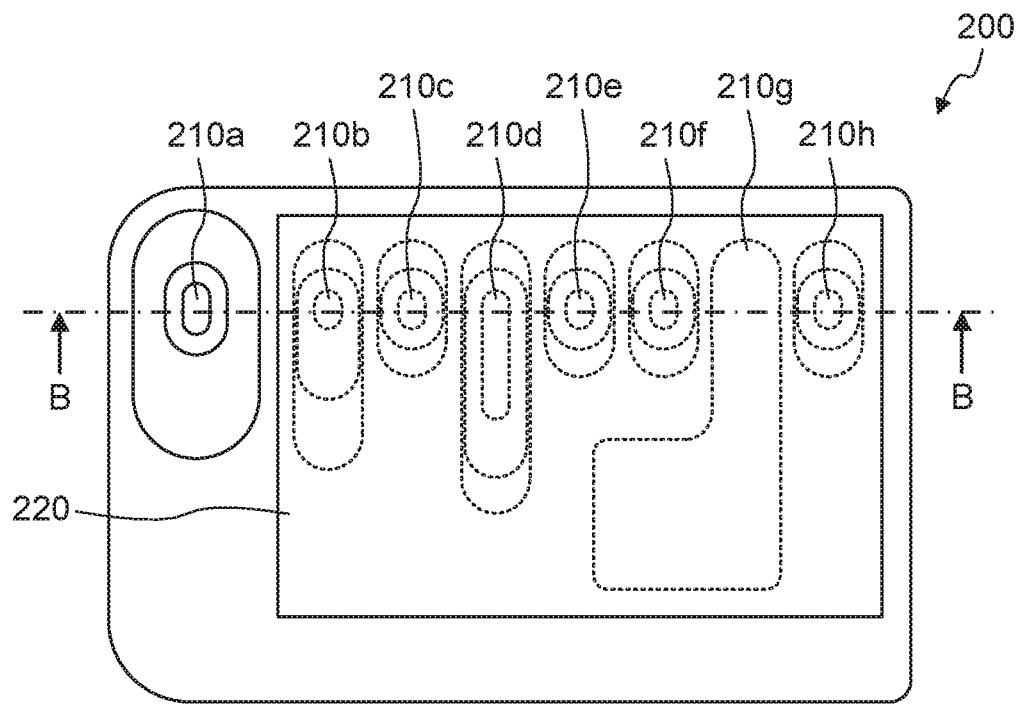
FIG. 4A is a plan view of a reagent chip.
Figure 4B:
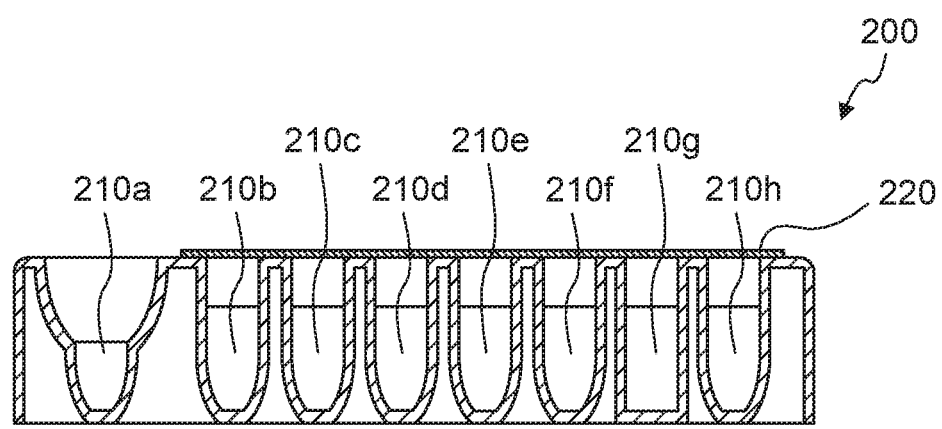
FIG. 4B is a cross-sectional view taken along line B-B in FIG. 4A.

FIG. 4A is a plan view of reagent chip 200, and FIG. 4B is a cross-sectional view taken along line B-B in FIG. 4A. In these figures, liquids contained in several vessels are omitted. As shown in FIGS. 4A and 4B, reagent chip 200 includes a plurality of vessels 210a to 210h, and first film 220 that closes openings of some of vessels 210b to 210h among the plurality of vessels 210a to 210h.

The plurality of vessels 210a to 210h are bottomed recesses configured to be able to contain a liquid (e.g., a specimen, a reagent, waste liquid, and the like). In the present embodiment, reagent chip 200 has eight vessels 210a to 210h. First vessel 210a to contain a specimen and a seventh vessel 210g to collect waste liquid are empty in a state before use, while different reagents are respectively contained in second vessel 210b, third vessel 210c, fourth vessel 210d, fifth vessel 210e, sixth vessel 210f, and eighth vessel 210h that are for storage of various reagents. A type of the reagent is not particularly limited, and is appropriately selected depending on use of reagent chip 200. Each of vessels 210b to 210f and 210h of reagent chip 200 according to the present embodiment to be used for SPFS contains for example, a saline solution for dilution of a specimen; a buffer solution to clean channel 370 of channel chip 300; a fluorescent labeling solution containing a fluorescently labeled antibody to fluorescently label a substance to be detected captured by a reaction field; a buffer solution to fill an inside of channel 370 at a time of fluorescent measurement, and the like.

A material forming each of vessels 210a to 210h is not particularly limited as long as the vessel can hold a liquid and does not react with the contained liquid. The material forming the plurality of vessels 210a to 210h is, for example, resin, glass, metal, or the like. Examples of resins include polypropylene (PP), polystyrene (PS), acrylic resin, cycloolefin polymer (COP), polyethylene (PE), and polycarbonate (PC).

A shape and a size of each of vessels 210a to 210h is not particularly limited as long as pipette tip 420 can be inserted at a predetermined depth as will be described later (see FIG. 7A), and is appropriately selected in accordance with a type and an amount of a reagent to be contained inside. In the present embodiment, first vessel 210a to contain a specimen (e.g., blood) provided by a user and seventh vessel 210g to collect waste liquid are larger than other vessels b to f and h. Further, the vessels a to f and h from which reagents contained inside are sucked by pipette 400 have a shape with a cross sectional area in a horizontal direction becoming smaller as approaching a bottom in order to facilitate suction of a reagent. Further, in the present embodiment, the plurality of vessels 210a to 210h are integrally formed by injection molding or the like.

First film 220 hermetically seals openings of second vessel 210b, third vessel 210c, fourth vessel 210d, fifth vessel 210e, sixth vessel 210f, seventh vessel 210g, and eighth vessel 210h. Even if reagents are contained in these vessels 210b to 210h before use, spillage of the reagent from each of vessels 210b to 210h is prevented by first film 220. Further, as will be described later, although one or two or more through holes are formed in first film 220 after use, spillage of the reagent or waste liquid in these vessels 210b to 210h can also be prevented to some extent by first film 220.

A material and a thickness of first film 220 are not particularly limited as long as first film 220 can seal vessels 210b to 210h and can be penetrated by pipette tip 420. Examples of a material of first film 220 include polyethylene terephthalate (PET), aluminum, (AL), polyethylene (PE), low-density polyethylene (LDPE), linear low-density polyethylene (LLDPE), biaxially oriented polypropylene (OPP), casting polypropylene (CPP), nylon (NY), and ethylene-vinyl acetate copolymer (EVA). A thickness of first film 220 is, for example, 10 to 200 μm. Further, first film 220 may be a laminate body of a plurality of films. Examples of the laminated film include overprint coating 1 μm/AL 20 μm/sealant film 35 μm, OP coat 3 μm/AL 30 μm/CPP 3 μm, and PET 14 μm/AL 20 μm/sealant film 8 μm. Examples of a material of the sealant film include polyethylene (PE), low-density polyethylene (LDPE), linear low-density polyethylene (LLDPE), biaxially oriented polypropylene (OPP), casting polypropylene (CPP), ethylene-vinyl acetate copolymer (EVA), and polyvinyl chloride (PVC).

Means to join first film 220 to vessels 210b to 210h is not particularly limited as long as it is possible to seal vessels 210b to 210h and to secure a joining strength to an extent that peeling does not occur when pipette tip 420 is pierced into first film 220. For example, first film 220 is joined to vessels 210b to 210h by fusion bonding, double-sided adhesive tape, or the like.

(Channel Chip)

Figure 5:
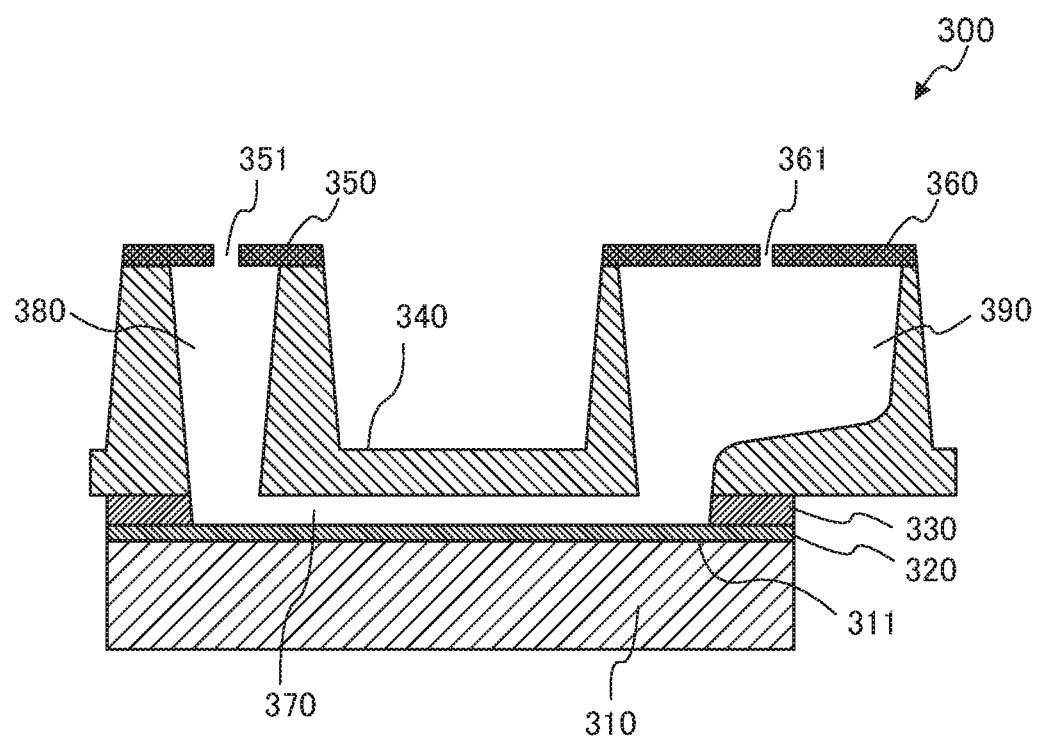
FIG. 5 is a cross-sectional view of a channel chip.

FIG. 5 is a cross-sectional view of channel chip 300. As shown in FIG. 5, channel chip 300 has prism 310, metal film 320, adhesive layer 330, channel lid 340, second film 350, and third film 360.

As will be described later, channel chip 300 also has channel 370, pipette tip insertion part 380 connected to one end of channel 370, and storage part 390 connected to the other end of channel 370. Second film 350 closes an opening of pipette tip insertion part 380, and third film 360 closes an opening of storage part 390. The components of channel chip 300 other than channel 370, pipette tip insertion part 380, and second film 350 are not indispensable components of channel chip 300, but are appropriately omitted depending on use. For example, although prism 310 and metal film 320 are indispensable components to implement prism-coupling SPFS (PC-SPFS), prism 310 and metal film 320 can be replaced with another member (e.g., a resin plate) in a case where the PC-SPFS is not implemented. Further, storage part 390 is an indispensable component to perform reciprocating liquid delivery, but storage part 390 can be omitted in a case where reciprocating liquid delivery is not performed. Further, although third film 360 is provided to prevent scattering of a liquid from storage part 390, third film 360 can be omitted if it is not necessary.

Prism 310 is made of a dielectric transparent to excitation light used in SPFS, and has at least an incident surface, reflection surface 311, and an exit surface. The incident surface is a surface to allow excitation light to enter into prism 310. Reflection surface 311 is a surface formed with metal film 320 thereon, and excitation light entering into prism 310 is totally reflected at reflection surface 311 (an interface between prism 310 and metal film 320). The exit surface is a surface to allow the reflected light reflected by reflection surface 311 to exit outside prism 310. It should be noted that, FIG. 5 does not illustrate the incident surface and the exit surface since they are located in front of or behind the page.

A shape of prism 310 is not particularly limited. In the present embodiment, the shape of prism 310 is a columnar body having a trapezoid as a bottom surface. A surface corresponding to one base of the trapezoid is reflection surface 311, a surface corresponding to one leg is the incident surface, and a surface corresponding to another leg is the exit surface. A material of prism 310 is not particularly limited as long as it is a dielectric transparent to excitation light. Examples of a material of prism 310 include resin and glass. The material of prism 310 is preferably a resin having a refractive index of 1.4 to 1.6 and a small birefringence.

Metal film 320 is disposed on the reflection surface 311 of prism 310. Disposing metal film 320 on reflection surface 311 of prism 310 causes an interaction (SPR) between photons of excitation light incident on reflection surface 311 under a total reflection condition and free electrons in metal film 320, generating an enhanced electric field on a surface of metal film 320.

A material of metal film 320 is not particularly limited as long as it is a metal capable of generating SPR. Examples of a material of metal film 320 include gold, silver, copper, aluminum, and alloys of these. A method of forming metal film 320 is not particularly limited. Examples of a method of forming metal film 320 include sputtering, vapor deposition, and plating. A thickness of metal film 320 is not particularly limited, but it is preferably within a range of 30 to 70 nm.

Adhesive layer 330 bonds prism 310 or metal film 320 to channel lid 340. Adhesive layer 330 is, for example, a double-sided adhesive tape. Further, adhesive layer 330 also serves to define a side surface shape of channel 370. That is, adhesive layer 330 is provided with an elongated through hole, and channel 370 is formed with one end being open to pipette tip insertion part 380 described later and the other end being open to storage part 390 described later, by closing a lower opening of the through hole with prism 310 or metal film 320, and closing an upper opening with channel lid 340. Meanwhile, prism 310 or metal film 320 may be joined to channel lid 340 by welding or pressure bonding without using adhesive layer 330. In this case, a groove having a shape corresponding to channel 370 may be provided on a lower surface of channel lid 340, and the side surface shape of channel 370 may be defined by this groove.

Channel lid 340 is disposed on adhesive layer 330 (in a case where adhesive layer 330 is omitted, prism 310 or metal film 320). Channel lid 340 is formed with two through holes. By closing a lower opening of one through hole with prism 310 or metal film 320, and closing an upper opening with second film 350, this through hole becomes pipette tip insertion part 380. By closing a lower opening of the other through hole with prism 310 or metal film 320, this through hole becomes storage part 390. In the present embodiment, in order to prevent scattering of a liquid from storage part 390, the opening of storage part 390 (an upper opening of the other through hole) is closed with third film 360.

A shape and a size of pipette tip insertion part 380 is not particularly limited as long as pipette tip 420 can be inserted at a predetermined depth as will be described later (see FIG. 7B). From the viewpoint of efficiently introducing a liquid in pipette tip 420 into channel 370, the size of pipette tip insertion part 380 is preferably not too large relative to pipette tip 420.

Whereas, a shape and a size of storage part 390 is not particularly limited as long as a volume of storage part 390 exceeds a volume of a liquid at a time of reciprocation of the liquid in channel 370.

Channel lid 340 is formed of a material transparent to light (e.g., fluorescence) detected by SPFS. However, a part of channel lid 340 may be formed of a material opaque to light as long as detection of light is not obstructed. Further, in a case of using channel chip 300 for other application such as the SPR method, channel lid 340 may be formed of a material opaque to light.

Examples of a material transparent to light include resin. A material forming channel lid 340 is, for example, resin, glass, or the like. Examples of resins include polypropylene (PP), polystyrene (PS), acrylic resin, cycloolefin polymer (COP), polyethylene (PE), and polycarbonate (PC).

In the present embodiment, a capturing body to capture a substance to be detected that is a detection target of SPFS is fixed to metal film 320 exposed in channel 370. The capturing body is a substance having a recognition site to specifically bind to a substance to be detected in a specimen. In a case where the capturing body is fixed in channel 370, the substance to be detected is selectively bound to the capturing body when a specimen or its diluted liquid is injected into channel 370. That is, a region fixed with the capturing body becomes a reaction field, and the substance to be detected is captured by the reaction field. In SPFS, a reaction of labeling a substance to be detected captured by the capturing body with a fluorescent substance is also performed in this reaction field. Detecting the fluorescence emitted from this fluorescent substance enables detection of the substance to be detected.

A type of the capturing body is not particularly limited as long as the capturing body has a recognition site to specifically bind to a substance to be detected. Examples of the capturing body include an antibody or a fragment thereof capable of specifically binding to a substance to be detected, an enzyme capable of specifically binding to a substance to be detected, and the like. A width and a height of channel 370 are not particularly limited, and are appropriately selected depending on use or the like of channel chip 300.

Second film 350 closes an upper opening of pipette tip insertion part 380. Second film 350 is a film that can be pierced by pipette tip 420 and can come into close contact with an outer surface of pipette tip 420 without a gap when pipette tip 420 is pierced. For example, second film 350 is an elastic film. Examples of a material forming second film 350 include synthetic rubbers such as silicone rubber, urethane rubber, and fluorinated rubber; and elastic resins such as polyurethane, low-density polyethylene (LDPE), and linear low-density polyethylene (LLDPE). Second film 350 may be a laminate body of a plurality of films. In addition, second film 350 may be provided with fine through hole 351 to facilitate piercing of pipette tip 420. That is, second film 350 may be provided with through hole 351 before pipette tip 420 is first inserted.

Means to join second film 350 to channel lid 340 is not particularly limited as long as a joining strength can be secured to an extent that peeling does not occur when pipette tip 420 is pierced into second film 350. For example, second film 350 is joined to channel lid 340 by an adhesive, a double-sided adhesive tape, fusion bonding, or the like.

Third film 360 closes an upper opening of storage part 390. Third film 360 has fine vent hole 361. A configuration of third film 360 is not particularly limited. For example, third film 360 may be an elastic film similar to second film 350 described above. Means to join third film 360 to channel lid 340 is not particularly limited. For example, third film 360 is joined to channel lid 340 by an adhesive, a double-sided adhesive tape, fusion bonding, or the like.

As will be described later, pipette tip 420 is inserted to a predetermined depth into pipette tip insertion part 380 (see FIG. 7B). At this time, second film 350 is in contact with an outer periphery of pipette tip 420 without a gap. Therefore, injecting a liquid into pipette tip insertion part 380 from pipette tip 420 enables the liquid to be introduced into channel 370, and sucking a liquid in pipette tip insertion part 380 into pipette tip 420 enables the liquid in channel 370 to be removed. Further, alternately injecting and sucking a liquid also allows reciprocation of the liquid in channel 370 (reciprocating liquid delivery).

Figure 7A:
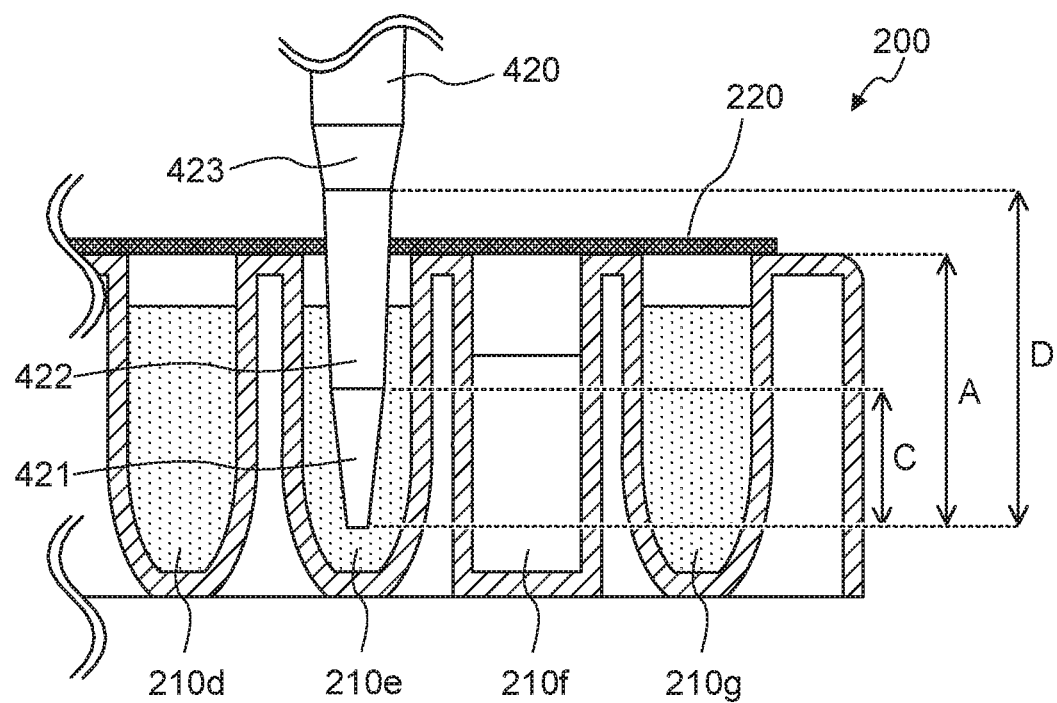
FIG. 7A is a schematic view showing a state where the pipette tip is inserted into a vessel of the reagent chip.
Figure 7B:
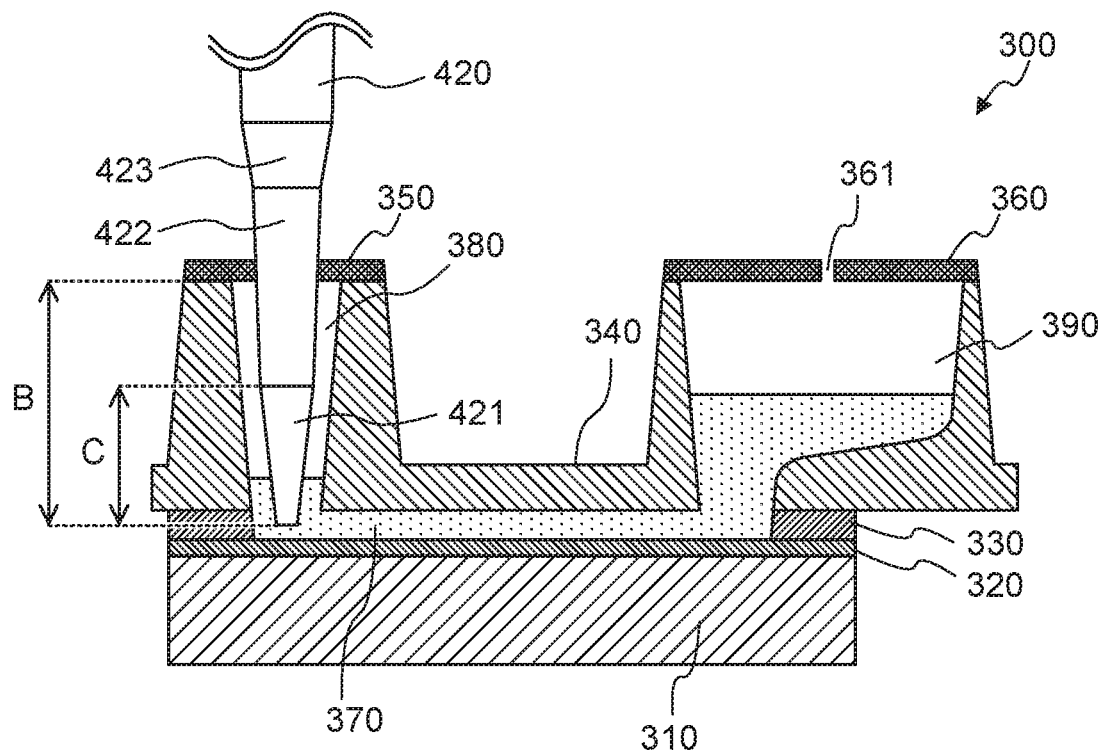
FIG. 7B is a schematic view showing a state where the pipette tip is inserted into a pipette tip insertion part of the channel chip.

When a liquid of an amount exceeding a volume of channel 370 is introduced into channel 370 from pipette tip insertion part 380, the liquid flows into storage part 390 from channel 370 (see FIG. 7B). Further, also in a case of reciprocatingly moving a liquid in channel 370, the liquid flows into storage part 390. The liquid flowing into storage part 390 is stirred in storage part 390. When the liquid is stirred in storage part 390, a concentration of a component (e.g., a substance to be detected or a cleaning component) of a liquid (e.g., a specimen or a cleaning liquid) passing through channel 370 becomes uniform, causing various reactions to be likely to occur in channel 370, or enhancing a cleaning effect.

It should be noted that, FIGS. 3 to 5 illustrate an aspect where reagent chip 200 and channel chip 300 are separate from each other, but reagent chip 200 and channel chip 300 may be integrated. For example, reagent chip 200 and channel chip 300 may be integrated by fitting reagent chip 200 and channel chip 300 into a separately prepared frame.

(Pipette)

Pipette 400 sucks a liquid (e.g., a specimen or a reagent) in vessels 210a to 210f and 210h of reagent chip 200, and injects the sucked liquid into channel 370 of channel chip 300. Thereafter, if necessary, pipette 400 causes reciprocation of the liquid in channel 370 by alternately repeating suction and injection of the liquid in channel 370. Further, pipette 400 sucks the liquid in channel 370 of channel chip 300 to remove the liquid in channel 370, and injects the sucked liquid (waste liquid) into seventh vessel 210g (waste liquid vessel) of the reagent chip.

Pipette 400 has pipette nozzle 410 and pipette tip 420 attached to a distal end of pipette nozzle 410 (see FIG. 3). Normally, pipette 400 also has a syringe pump (not shown) connected to pipette nozzle 410, a driving device (not shown) of the syringe pump, a moving device (not shown) of pipette nozzle 410, and the like. The driving device of the syringe pump is a device to cause reciprocating motion of a plunger of the syringe pump and includes, for example, a stepping motor. The reciprocating motion of the plunger in the syringe pump quantitatively causes suction of a liquid into pipette tip 420 and discharge of a liquid from inside pipette tip 420. The moving device of pipette nozzle 410 freely moves pipette nozzle 410 vertically and horizontally. The moving device of pipette nozzle 410 is formed by, for example, a driving device including a stepping motor, a robot arm, a biaxial stage, or a vertically movable turntable.

Pipette tip 420 is used with its proximal end attached on pipette nozzle 410. Since the distal end of pipette tip 420 is inserted into vessels 210a to 210h of reagent chip 200 and pipette tip insertion part 380 of channel chip 300, the distal end is formed to be thinner than other parts. Whereas, the proximal end of pipette tip 420 is formed thicker than other parts since the proximal end of pipette tip 420 is to be inserted with pipette nozzle 410 inside thereof. Therefore, as a whole, pipette tip 420 has a shape that is thickened from the distal end side toward the proximal end side. Further, the shape of pipette tip 420 is rotationally symmetric (preferably circularly symmetric) with an axis along suction and discharge directions of a liquid as a center axis. In the present embodiment, the shape of pipette tip 420 is circularly symmetric except for a rib to be described later, and a cross-sectional shape orthogonal to the axis of pipette tip 420 is circular on both an outer surface and an inner surface.

Figure 6A:
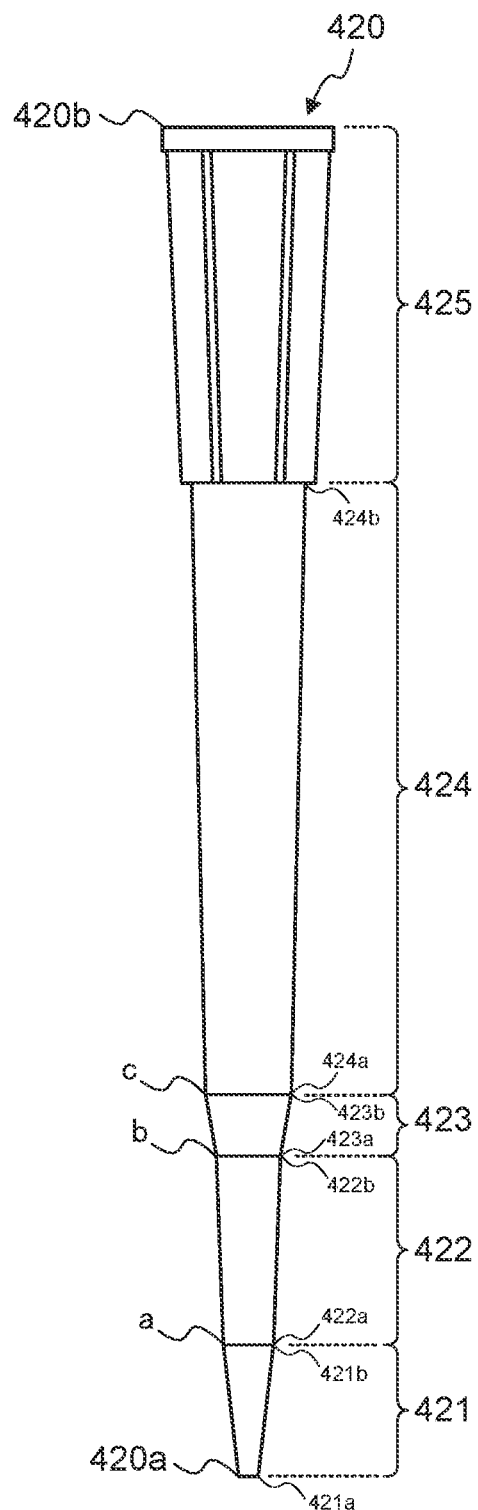
FIG. 6A is a front view of a pipette tip according to an embodiment of the present invention.
Figure 6B:
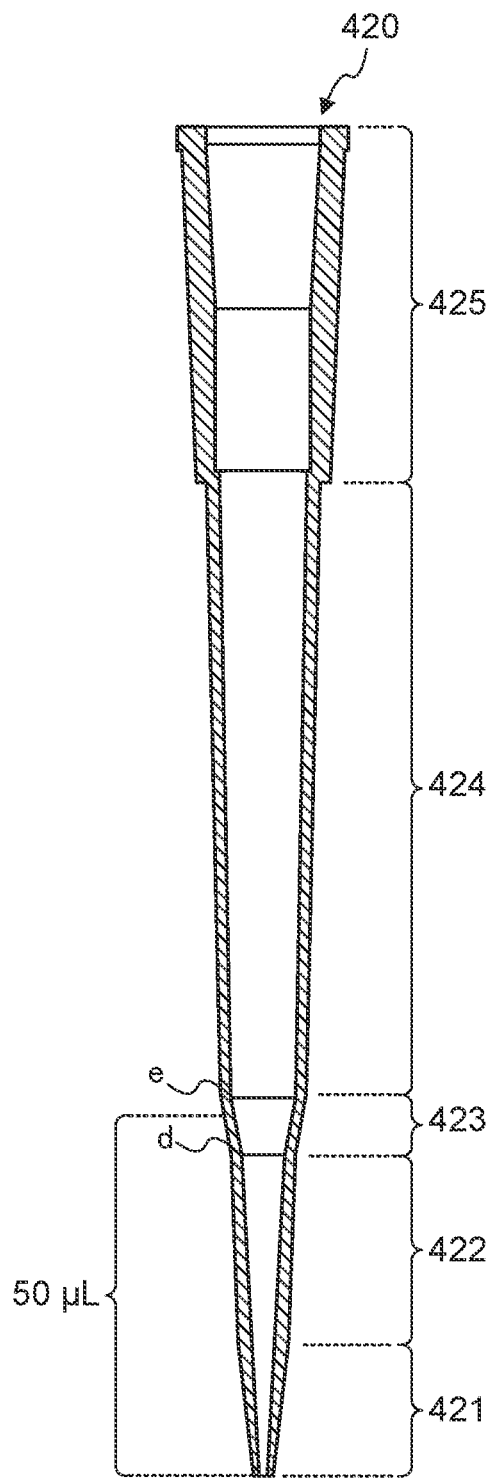
FIG. 6B is a cross-sectional view including a center axis of the pipette tip.

FIG. 6A is a front view of pipette tip 420 according to the present embodiment, and FIG. 6B is a cross-sectional view including a center axis of pipette tip 420 according to the present embodiment. As shown in these figures, pipette tip 420 according to the present embodiment has the distal and proximal ends 420a and 420b and includes, in order from the distal end side toward the proximal end side, first part 421 having the first distal and proximal ends 421a and 421b, second part 422 having the second distal and proximal ends 422a and 422b, third part 423 having the third distal and proximal ends 423a and 423b, fourth part 424 having the fourth distal and proximal ends 424a and 424b, and fifth part 425.

First part 421 includes the distal end of pipette tip 420 and is a portion where an outer diameter gradually increases from a distal end side toward a proximal end side. The outer diameter of the distal end is not particularly limited as long as the distal end can be inserted into vessels 210a to 210h of reagent chip 200 and pipette tip insertion part 380 of channel chip 300. The outer diameter of the distal end of pipette tip 420 is, for example, 0.8 to 2.5 nm. An outer diameter of the proximal end of first part 421 is, for example, 1.2 to 3.0 mm. A length along an axial direction of first part 421 is not particularly limited, but as will be described later, the length is preferably set such that second part 422 can be positioned at the same height as first film 220 (see FIG. 7A) when pipette tip 420 is inserted deepest into vessels 210b to 210h of reagent chip 200, and second film 350 can be in contact with second part 422 (see FIG. 7B) when pipette tip 420 is inserted deepest into pipette tip insertion part 380 of channel chip 300. The length along the axial direction of first part 421 is, for example, 3 to 13 mm. A taper angle of an outer surface of first part 421 is, for example, 8° or more and less than 40°. Increasing the taper angle of the outer surface of first part 421 located on the most distal end side in this way allows the outer diameter of the most part of pipette tip 420 excluding the vicinity of the distal end to be equal to or larger than a size required for second film 350 to come into close contact with the outer surface of pipette tip 420 without a gap. As a result, even when the position of pipette tip 420 is shifted to some extent when pipette tip 420 is inserted into pipette tip insertion part 380 of channel chip 300, second film 350 can come into close contact with the outer surface of pipette tip 420 without a gap, making it possible to properly perform injection of a liquid into channel 370 and suction of a liquid from channel 370. In this specification, the term "taper angle" means an angle formed by two straight lines constituting a cross section of a target inclined surface (truncated conical surface) in a cross section including the center axis of pipette tip 420.

Second part 422 is arranged adjacent to first part 421 on the proximal end side, and is a portion where an outer diameter does not change or gradually increases from a distal end side toward a proximal end side. A taper angle of an outer surface of second part 422 is smaller than the taper angle of the outer surface of first part 421. An outer diameter of the distal end of second part 422 is the same as the outer diameter of the proximal end of first part 421, and is, for example, 1.2 to 3.0 mm. An outer diameter of the proximal end of second part 422 is, for example, 1.25 to 4.0 mm. A length along an axial direction of second part 422 is not particularly limited, but as will be described later, the length is preferably set such that second part 422 can be positioned at the same height as first film 220 (see FIG. 7A) when pipette tip 420 is inserted deepest into vessels 210b to 210h of reagent chip 200, and second film 350 can be in contact with second part 422 (see FIG. 7B) when pipette tip 420 is inserted deepest into pipette tip insertion part 380 of channel chip 300. The length along the axial direction of second part 422 is, for example, 3 to 20 mm. The taper angle of second part 422 is, for example, 0.5° or more and 5° or less. In order to hermetically seal pipette tip insertion part 380 with second part 422 and with second film 350 when pipette tip 420 is inserted into pipette tip insertion part 380 of channel chip 300, it is preferable that the outer diameter of second part 422 does not greatly change from the distal end side to the proximal end side, and the taper angle of the outer surface of second part 422 is preferably 5° or less. Setting the taper angle of the outer surface of second part 422 to 5° or less also enables suppression of the size of the through hole formed in first film 220 when pipette tip 420 is inserted into vessels 210b to 210h of reagent chip 200. As described above, the outer surface of second part 422 need not be inclined with respect to the center axis of pipette tip 420, but is preferably slightly inclined from the viewpoint of mold releasing.

Third part 423 is arranged adjacent to second part 422 on the proximal end side, and is a portion where an outer diameter gradually increases from a distal end side toward a proximal end side. A taper angle of an outer surface of third part 423 is larger than the taper angle of the outer surface of first part 421 and second part 422. An outer diameter of the distal end of third part 423 is the same as the outer diameter of the proximal end of second part 422, and is, for example, 1.25 to 4.0 mm. An outer diameter of the proximal end of third part 423 is, for example, 3.0 to 10.0 mm. A length along an axial direction of third part 423 is, for example, 1 to 15 mm. The taper angle of third part 423 is, for example, 10° or more and 40° or less. Increasing the taper angle of the outer surface of third part 423 in this way allows a volume of pipette tip 420 to be increased.

Fourth part 424 is arranged adjacent to third part 423 on the proximal end side, and is a portion where an outer diameter does not change or gradually increases from a distal end side toward a proximal end side. A taper angle of an outer surface of fourth part 424 is smaller than the taper angle of the outer surface of third part 423. The outer diameter of the distal end of fourth part 424 is the same as the outer diameter of the proximal end of third part 423, and is, for example, 5.0 to 10.0 mm. An outer diameter of the proximal end of fourth part 424 is set in accordance with a shape of pipette nozzle 410, and is, for example, 5.0 to 15.0 mm. A length along an axial direction of fourth part 424 is not particularly limited. The taper angle of fourth part 424 is, for example, 0.5° or more and less than 40°. Reducing the taper angle of the outer surface of fourth part 424 in this way enables suppression of an increase in an outer diameter and an inner diameter of fifth part 425 to be fitted with pipette nozzle 410. This can prevent an increase of the size of pipette nozzle 410 and accordingly an increase of the size of the entire liquid delivery system 100 including pipette 400. As described above, the outer surface of fourth part 424 needs not be inclined with respect to the center axis of pipette tip 420, but is preferably inclined from the viewpoint of mold releasing.

Fifth part 425 is a portion to be inserted with pipette nozzle 410. Fifth part 425 is arranged adjacent to fourth part 424 on the proximal end side, and the outer diameter and the inner diameter gradually increase from a distal end side to a proximal end side in correspondence to the shape of pipette nozzle 410. A taper angle of an outer surface and of an inner surface of fifth part 425 is set in accordance with the shape of pipette nozzle 410. In the present embodiment, the outer surface of fifth part 425 is provided with a rib to increase the strength. Meanwhile, in the present embodiment, fifth part 425 is an inserted part of pipette nozzle 410, but the inserted part of pipette nozzle 410 need not be adjacent to fourth part 424. For example, even in pipette tip 420 of this embodiment, a portion having a taper angle different from that of fourth part 424 and fifth part 425 may be further inserted between fourth part 424 and fifth part 425 (the inserted part of pipette nozzle 410).

As described above, first part 421 and second part 422 are adjacent to each other, and the taper angle of the outer surface of second part 422 is smaller than the taper angle of the outer surface of first part 421. Therefore, at a boundary between first part 421 and second part 422, an inflection part (corner) a having a convex shape with respect to the outer side is provided. Further, second part 422 and third part 423 are adjacent to each other, and the taper angle of the outer surface of third part 423 is larger than the taper angle of the outer surface of second part 422. Therefore, at a boundary between second part 422 and third part 423, an inflection part (corner) b having a concave shape with respect to the outer side is provided. Further, third part 423 and fourth part 424 are adjacent to each other, and the taper angle of the outer surface of fourth part 424 is smaller than the taper angle of the outer surface of third part 423. Therefore, at a boundary between third part 423 and fourth part 424, an inflection part (corner) c having a convex shape with respect to the outer side is provided. Meanwhile, these inflection parts a to c may be chamfered or not chamfered.

FIG. 7A is a schematic view showing a state where pipette tip 420 is inserted into fifth vessel 210e of reagent chip 200. FIG. 7B is a schematic view showing a state where pipette tip 420 is inserted into pipette tip insertion part 380 of channel chip 300.

In liquid delivery system 100 according to the present embodiment, when A is a length along the axial direction of pipette tip 420 from the distal end of pipette tip 420 to a lower surface of first film 220 when pipette tip 420 is inserted into vessels 210b to 210f and 210h of reagent chip 200 in order to suck a liquid in vessels 210b to 210f and 210h of reagent chip 200 as shown in FIG. 7A, and B is a length along the axial direction of pipette tip 420 from the distal end of pipette tip 420 to a lower surface of second film 350 when pipette tip 420 is inserted into pipette tip insertion part 380 of channel chip 300 in order to inject a liquid into channel 370, or to suck a liquid in channel 370 as shown in FIG. 7B, A>B is satisfied. That is, in liquid delivery system 100 according to the present embodiment, pipette tip 420 is inserted deeper in a case of inserting pipette tip 420 into vessels 210b to 210f and 210h of reagent chip 200 as compared with a case of inserting into pipette tip insertion part 380 of channel chip 300.

It should be noted that the above A and B mean the lengths when pipette tip 420 is inserted deepest into vessels 210b to 210f and 210h or pipette tip insertion part 380. From the viewpoint of reducing an amount of remaining liquid, in sucking a liquid into pipette tip 420, the distal end of pipette tip 420 is preferably close to the bottoms of vessels 210b to 210f and 210h or pipette tip insertion part 380. However, if the distal end of pipette tip 420 is too close to the bottoms of vessels 210b to 210f and 210h or pipette tip insertion part 380, suction of the liquid is rather disabled. Therefore, suction of a liquid into pipette tip 420 is typically performed in a state where the distal end of pipette tip 420 is separated from the bottoms of vessels 210b to 210f and 210h or pipette tip insertion part 380. Similarly, injection of liquid into vessels 210b to 210h or pipette tip insertion part 380 is performed in a state where the distal end of pipette tip 420 is separated from the bottoms of vessels 210b to 210h or pipette tip insertion part 380. Meanwhile, a position of pipette tip 420 inserted into pipette tip insertion part 380 may be different between when injecting a liquid into channel 370 and when sucking a liquid in channel 370. In this case, the above B means a length when pipette tip 420 is inserted deeper into pipette tip insertion part 380. Pipette tip 420 is typically inserted deeper into pipette tip insertion part 380 when sucking a liquid in channel 370 than when injecting a liquid into channel 370. Similarly, a position of pipette tip 420 inserted into vessels 210b to 210h may be different between when sucking a liquid in vessels 210b to 210f and 210h and when discharging a liquid into vessels 210b to 210h. Pipette tip 420 is typically inserted shallower into vessels 210b to 210h when discharging a liquid into vessels 210b to 210h than when sucking a liquid in vessels 210b to 210f and 210h.

Further, as shown in FIG. 7A, in order to suck a liquid in vessels 210b to 210f and 210h of reagent chip 200, first film 220 is preferably positioned at the same height as second part 422 having a small taper angle when pipette tip 420 is inserted deepest into vessels 210b to 210f and 210h of reagent chip 200. That is, C<A is preferably satisfied where A is a length along the axial direction of pipette tip 420 from the distal end of pipette tip 420 to the lower surface of first film 220 when pipette tip 420 is inserted into vessels 210b to 210f and 210h of reagent chip 200, and C is a length along the axial direction of pipette tip 420 from the distal end of pipette tip 420 to the boundary between first part 421 and second part 422. Further, D>A is preferably satisfied where D is a length along the axial direction of pipette tip 420 from the distal end of pipette tip 420 to the boundary between second part 422 and third part 423. By inserting pipette tip 420 into vessels 210b to 210f and 210h such that first film 220 is positioned at the same height as second part 422 instead of first part 421, the liquid near the bottom of vessels 210b to 210f and 210h can also be sucked. Further, by inserting pipette tip 420 into vessels 210b to 210f and 210h such that first film 220 is positioned at the same height as second part 422 having a small taper angle instead of third part 423 having a large taper angle, the size of the through hole formed in first film 220 by inserting pipette tip 420 can be suppressed.

From the viewpoint of suppressing the size of the through hole formed in first film 220, a maximum outer diameter of a portion of length A from the distal end of pipette tip 420 is preferably 3 mm or less. This causes a maximum diameter of the through hole formed in first film 220 to be 4 mm or less. It should be noted that, the reason why the inner diameter of the through hole is larger than the outer diameter of pipette tip 420 is that a crack or the like may occur around the through hole.

Further, as shown in FIG. 7B, second film 350 preferably comes into contact with second part 422 having a small taper angle when pipette tip 420 is inserted deepest into pipette tip insertion part 380 of channel chip 300 in order to inject a liquid into channel 370, or to suck a liquid in channel 370. That is, C<B is preferably satisfied where B is a length along the axial direction of pipette tip 420 from the distal end of pipette tip 420 to the lower surface of second film 350 when pipette tip 420 is inserted into pipette tip insertion part 380 of channel chip 300, and C is a length along the axial direction of pipette tip 420 from the distal end of pipette tip 420 to the boundary between first part 421 and second part 422. Moreover, D>B is also satisfied when D>A is satisfied as described above, since A>B. By inserting pipette tip 420 into pipette tip insertion part 380 such that second film 350 comes into contact with second part 422 having an outer diameter that is large to some extent instead of first part 421 having a small outer diameter, second film 350 easily comes into close contact with the outer surface of pipette tip 420 without a gap, Further, by inserting pipette tip 420 into pipette tip insertion part 380 such that second film 350 comes into contact with second part 422 having a small taper angle instead of third part 423 having a large taper angle, second film 350 easily comes into close contact with the outer surface of pipette tip 420 without a gap.

As described above, the outer surface of first part 421 and the outer surface of second part 422 have different taper angles from each other, the outer surface of second part 422 and the outer surface of third part 423 also have different taper angles from each other, and the outer surface of third part 423 and the outer surface of fourth part 424 also have different taper angles from each other. Therefore, on the outer surface of pipette tip 420, there are three inflection parts (corners) "a" to "c" between from the distal end of pipette tip 420 to the proximal end of fourth part 424. Meanwhile, the taper angle of the outer surface of pipette tip 420 does not have to coincide with the taper angle of the inner surface. The taper angle of the outer surface of pipette tip 420 is set in consideration of a positional relationship between first film 220 and second film 350 as described above, but the taper angle of the inner surface of pipette tip 420 is set in consideration of quantitativeness at a time of suction and discharge of a liquid.

From the viewpoint of improving the quantitativeness at a time of suction and discharge of a liquid, the number of inflection parts (corners) on the inner surface of pipette tip 420 is preferably small. Specifically, it is preferable that the number of inflection parts (corners) on the inner surface in a portion from the distal end of pipette tip 420 to the proximal end of fourth part 424 is 0 to 2. In a case where the number of inflection parts is 0, the taper angle from the distal end of pipette tip 420 to the proximal end of fourth part 424 is constant. In a case where the number of inflection parts is one or two, the taper angle changes one or two times from the distal end of pipette tip 420 to the proximal end of fourth part 424. In the present embodiment, there are two inflection parts "d" and "e" between from the distal end of pipette tip 420 to the proximal end of fourth part 424. Specifically, the taper angle of the inner surface of second part 422 is the same as the taper angle of the inner surface of first part 421. Therefore, there is no inflection part (corner) at the boundary between first part 421 and second part 422. Further, the taper angle of the inner surface of third part 423 is larger than the taper angle of the inner surface of second part 422. Therefore, at the boundary between second part 422 and third part 423, the inflection part (corner) "d" having a convex shape with respect to the inner side is provided. Further, the taper angle of the inner surface of fourth part 424 is smaller than the taper angle of the inner surface of third part 423. Therefore, at the boundary between third part 423 and fourth part 424, the inflection part (corner) "e" having a concave shape with respect to the inner side is provided. Meanwhile, these inflection parts "d" and "e" may be chamfered or not chamfered.

Further, liquid droplets tend to remain in an inflection part (corner) having a concave shape with respect to inside on the inner surface of pipette tip 420, which tends to lower quantitativeness at a time of suction and discharge of a liquid. Therefore, from the viewpoint of improving the quantitativeness during suction and discharge of a liquid, it is preferable that the number of the inflection parts having a concave shape with respect to inside on the inner surface of pipette tip 420 is particularly small. Specifically, the number of the inflection parts having a concave shape with respect to inside on an inner surface of a portion from the distal end of pipette tip 420 to the proximal end of fourth part 424 (an inflection part where the taper angle of the inner surface decreases from the distal end side toward the proximal end side) is preferably zero or one. In the present embodiment, between from the distal end of pipette tip 420 to the proximal end of fourth part 424, only one inflection part having a concave shape with respect to inside is provided at the boundary between third part 423 and fourth part 424 (inflection part "e").

Further, from the viewpoint of improving quantitativeness at a time of suction and discharge of liquid, on an inner surface of a portion with a volume (a volume of an internal space) of 50 μL on the distal end side of pipette tip 420, it is preferable that there is no inflection part having a concave shape with respect to inside (an inflection part where the taper angle of the inner surface decreases from the distal end side toward the proximal end side). In the present embodiment, as shown in FIG. 6B, in the portion with a volume of 50 μL on the distal end side of pipette tip 420 corresponds to first part 421, second part 422, and a part of the distal end side of third part 423. Therefore, in the portion with a volume of 50 μL of the distal end side of pipette tip 420, there is no inflection part having a concave shape with respect to inside.

A material forming pipette tip 420 is not particularly limited. Pipette tip 420 is typically a resin-made disposable pipette tip. Examples of the resin forming pipette tip 420 include polypropylene (PP) and polystyrene (PS).

(Liquid Delivery Method)

Figure 8:
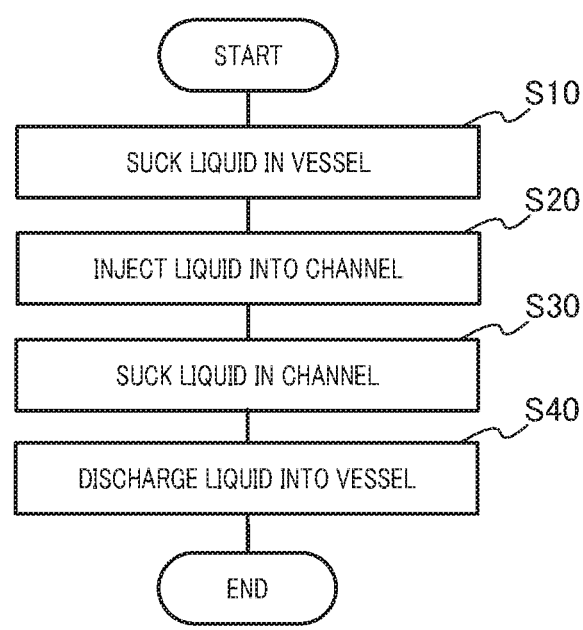
FIG. 8 is a flowchart for explaining an operation of the liquid delivery system according to the present embodiment.

Next, an operation of the liquid delivery system according to the present embodiment (the liquid delivery method according to the present embodiment) will be described. FIG. 8 is a flowchart for explaining an operation of the liquid delivery system according to the present embodiment (the liquid delivery method according to the present embodiment).

First, a reagent contained in any one of vessels 210b to 210f and 210h of reagent chip 200 is sucked into pipette tip 420 (step S10). Specifically, first, pipette tip 420 is pierced into first film 220, and pipette tip 420 is inserted into vessels 210b to 210f and 210h to a predetermined depth (see FIG. 7A). As described above, it is preferable to insert pipette tip 420 into vessels 210b to 210f and 210h such that first film 220 is positioned at the same height as second part 422, that is, the above expression of C<A<D (see FIG. 7A) is satisfied. In this state, the liquid contained in vessels 210b to 210f and 210h is sucked into pipette tip 420. This makes it possible to properly suck the reagent in vessels 210b to 210f and 210h into pipette tip 420, while suppressing the size of the through hole formed in first film 220.

Next, the reagent sucked into pipette tip 420 in step S10 is injected into channel 370 of channel chip 300 (step S20). Specifically, first, pipette tip 420 is pierced into second film 350, and pipette tip 420 is inserted into pipette tip insertion part 380 to a predetermined depth (see FIG. 7B). As described above, it is preferable to insert pipette tip 420 into pipette tip insertion part 380 such that second film 350 comes into contact with second part 422, that is, the above expression of C<B<D (see FIG. 7B) is satisfied. In this state, when the liquid in pipette tip 420 is injected into pipette tip insertion part 380, the liquid is also injected into channel 370 since pressure inside pipette tip insertion part 380 increases.

This allows the liquid in pipette tip 420 to be properly injected into channel 370 in a state where second film 350 is in close contact with the outer surface of pipette tip 420 without a gap. Thereafter, in this state, the liquid may be reciprocated in channel 370 by repeating suction and discharge.

Next, the reagent injected into channel 370 in step S20 is sucked into pipette tip 420 (step S30). Specifically, first, pipette tip 420 is pierced into second film 350, and pipette tip 420 is inserted into pipette tip insertion part 380 to a predetermined depth (see FIG. 7B). As described above, it is preferable to insert pipette tip 420 into pipette tip insertion part 380 such that second film 350 comes into contact with second part 422, that is, the above expression of C<B<D (see FIG. 7B) is satisfied. Further, when step S30 is performed continuously with step S20, it is not necessary to insert pipette tip 420 into pipette tip insertion part 380 again since pipette tip 420 is still inserted in pipette tip insertion part 380. In this state, when the liquid in pipette tip insertion part 380 is sucked into pipette tip 420, the liquid in channel 370 is also sucked since pressure in pipette tip insertion part 380 decreases.

This allows the liquid in channel 370 to be properly sucked to pipette tip 420 in a state where second film 350 is in close contact with the outer surface of pipette tip 420 without a gap.

Finally, as an optional step, the reagent sucked into pipette tip 420 in step S30 is discharged into seventh vessel 210g of reagent chip 200 (step S40). Specifically, first, pipette tip 420 is pierced into first film 220, and pipette tip 420 is inserted into seventh vessel 210g to a predetermined depth. At this time, pipette tip 420 is inserted to a position equal to or less than a depth when pipette tip 420 is inserted into vessels 210b to 210f and 210h in step S10. In this state, the liquid in pipette tip 420 is discharged into seventh vessel 210g. This makes it possible to properly discharge the liquid in pipette tip 420 into seventh vessel 210g while suppressing the size of the through hole formed in first film 220.

According to the above procedure, it is possible to inject a reagent in vessels 210b to 210f and 210h into channel 370 of channel chip 300, and to remove a reagent in channel 370 of channel chip 300.

(Effect)

As described above, in pipette tip 420 according to the present embodiment, since the taper angle of the outer surface of first part 421 positioned on the most distal end side in pipette tip 420 is large, the outer diameter of the most part of pipette tip 420 is equal to or larger than a size required for second film 350 to come into close contact with the outer surface of pipette tip 420 without a gap. Therefore, when pipette tip 420 is inserted into pipette tip insertion part 380 of channel chip 300, second film 350 can come into close contact with the outer surface of pipette tip 420 without a gap, and injection of a liquid into channel 370 and suction of a liquid from channel 370 are properly performed.

In addition, in pipette tip 420 according to the present embodiment, since the taper angle of the outer surface of second part 422 positioned on the distal end side after first part 421 is small, the size of the through hole formed in first film 220 when pipette tip 420 is inserted into vessels 210b to 210h of reagent chip 200 is suppressed. This makes it difficult for a liquid in vessels 210b to 210h to spill.

In addition, in pipette tip 420 according to the present embodiment, since the taper angle of the outer surface of third part 423 positioned on the distal end side after first part 421 and second part 422 is large, the volume of pipette tip 420 can be increased. Whereas, since the taper angle of the outer surface of fourth part 424 positioned on the distal end side after third part 423 is small, an increase in the outer diameter and the inner diameter of fifth part 425 to be fitted with pipette nozzle 410 is suppressed. This prevents an increase of the size of pipette tip 420 and pipette nozzle 410, and accordingly prevents an increase of the size of the entire liquid delivery system 100 including pipette 400.

Therefore, according to liquid delivery system 100 according to the present embodiment, it is possible to properly perform a predetermined reaction in channel 370 of channel chip 300 with use of reagents in vessels 210$b$ to 210$f$ and 210$h$, and it is also possible to reduce the size of the through hole formed in first film 220 of vessels 210$b$ to 210$h$ so as to make it difficult for a liquid in vessels 210$b$ to 210$h$ to spill.

Meanwhile, in the present embodiment, the plurality of vessels 210$a$ to 210$h$ are integrated, but the number of vessels may be one, or the plurality of vessels may be separate bodies.

This application claims priority based on Japanese Patent Application No. 2016-146387 filed on Jul. 26, 2016. The contents described in the specification of the application and drawings are all incorporated herein by reference.

INDUSTRIAL APPLICABILITY

According to the pipette tip, the liquid delivery method, and the liquid delivery system of the present invention, it is possible to properly perform a predetermined reaction in the channel of the channel chip with use of a liquid in the vessel, and it is also possible to suppress the size of the through hole formed in the first film of the vessel and make it difficult for a liquid in the vessel to spill. For example, the pipette tip, the liquid delivery method, and the liquid delivery system according to the present invention are useful for clinical examination and the like.

REFERENCE SIGNS LIST 10 reagent chip
11 cleaning liquid vessel
12 specimen vessel
13 diluent vessel
14 sample liquid vessel
15 fluorescent labeling liquid vessel
16 pipette tip
20 inspection chip
21 channel
22 pipette tip insertion part
23 seal
30 sample injection part
31 reagent container
32 mineral oil container
33 reaction part
34 film
35 pipette tip
100 liquid delivery system
200 reagent chip
210$a$ first vessel
210$b$ second vessel
210$c$ third vessel
210$d$ fourth vessel
210$e$ fifth vessel
210$f$ sixth vessel
210$g$ seventh vessel
210$h$ eighth vessel
220 first film
300 channel chip
310 prism
311 reflection surface
320 metal film
330 adhesive layer
340 channel lid
350 second film
351 through hole
360 third film
361 vent hole
370 channel
380 pipette tip insertion part
390 storage part
400 pipette
410 pipette nozzle
420 pipette tip
421 first part
422 second part
423 third part
424 fourth part
425 fifth part
a convex inflection part between first part and second part
b concave inflection part between second part and third part
c convex inflection part between third part and fourth part

The invention claimed is:

1. A pipette tip to be attached to a pipette nozzle and used in a liquid delivery system performing:

a first step of sucking a liquid contained in a vessel into the pipette tip in a state where the pipette tip is inserted through a first film into the vessel of which opening is closed with the first film;

a second step of injecting the liquid retained in the pipette tip into a channel in a state where the pipette tip is inserted through a second film into a pipette tip insertion part of a channel chip having the channel and the pipette tip insertion part, the pipette tip insertion part being connected to one end of the channel and having an opening closed with the second film; and a third step of sucking the liquid in the channel into the pipette tip in a state where the pipette tip is inserted through the second film into the pipette tip insertion part of the channel chip, wherein A>B is satisfied where A is a length along an axial direction of the pipette tip from a distal end of the pipette tip to the first film when the pipette tip is inserted deepest into the vessel in the first step, and B is a length along the axial direction of the pipette tip from the distal end of the pipette tip to the second film when the pipette tip is inserted deepest into the pipette tip insertion part in the second step and the third step, the pipette tip comprising:

a first part that includes the distal end of the pipette tip and has an outer diameter gradually increasing from a first distal end of the first part toward a first proximal end of the first part;

a second part that is arranged adjacent to the first part on the first proximal end, has an outer diameter being unchanged or gradually increasing from a second distal end of the second part toward a second proximal end of the second part, and has a smaller taper angle of an outer surface than a taper angle of an outer surface of the first part, wherein the second part is longer than the first part;

a third part that is arranged adjacent to the second part on the second proximal end, has an outer diameter gradually increasing from a third distal end of the third part toward a third proximal end of the third part, and has a larger taper angle of an outer surface than the taper angle of the outer surface of the first part; and a fourth part that is arranged adjacent to the third part on the third proximal end, has an outer diameter being unchanged or gradually increasing from a fourth distal end of the fourth part toward a fourth proximal end of the fourth part, and has a smaller taper angle of an outer surface than the taper angle of the outer surface of the third part, wherein there is no inflection part, in which a taper angle of an inner surface of the pipette tip decreases, between the first part and the second part.

2. The pipette tip according to claim 1, wherein C<A is satisfied where C is a length along the axial direction of the pipette tip from the distal end of the pipette tip to a boundary between the first part and the second part.

3. The pipette tip according to claim 2, wherein D>A is satisfied where D is a length along the axial direction of the pipette tip from the distal end of the pipette tip to a boundary between the second part and the third part.

4. The pipette tip according to claim 3, wherein a maximum outer diameter of a portion of length A from the distal end of the pipette tip is 3 mm or less.

5. The pipette tip according to claim 3, wherein C<B is satisfied where B is a length along the axial direction of the pipette tip from the distal end of the pipette tip to the second film when the pipette tip is inserted deepest into the pipette tip insertion part in the second step and the third step.

6. The pipette tip according to claim 5, wherein the taper angle of the outer surface of the second part is 5° or less.

7. The pipette tip according to claim 1, wherein a maximum diameter, after removing the pipette tip, of a through hole formed in the first film by piercing the pipette tip into the first film in the first step is 4 mm or less.

8. The pipette tip according to claim 1, wherein the taper angle of the inner surface in a portion from the distal end of the pipette tip to the fourth proximal end of the fourth part is constant from the distal end of the pipette tip to the fourth proximal end of the fourth part, or changes one or two times between from the distal end of the pipette tip to the fourth proximal end of the fourth part.

9. The pipette tip according to claim 8, wherein a number of inflection parts in which the taper angle of the inner surface decreases from the distal end of the pipette tip to the fourth proximal end is 0 or 1 on the inner surface of the portion from the distal end of the pipette tip toward the fourth proximal end of the fourth part.

10. The pipette tip according to claim 9, wherein there is no inflection part in which the taper angle of the inner surface decreases from the first distal end toward a proximal end of a portion with a volume of 50 µL.

11. The pipette tip according to claim 1, wherein the second film has a through hole at a time point before the pipette tip is first inserted.

12. A liquid delivery method comprising:
a first step of sucking a liquid contained in a vessel into a pipette tip in a state where the pipette tip is inserted through a first film into the vessel of which opening is closed with the first film;
a second step of injecting the liquid retained in the pipette tip into a channel in a state where the pipette tip is inserted through a second film into a pipette tip insertion part of a channel chip having the channel and the pipette tip insertion part, the pipette tip insertion part being connected to one end of the channel and having an opening closed with the second film; and
a third step of sucking the liquid in the channel into the pipette tip in a state where the pipette tip is inserted through the second film into the pipette tip insertion part of the channel chip, wherein
A>B is satisfied where A is a length along an axial direction of the pipette tip from a distal end of the pipette tip to the first film when the pipette tip is inserted deepest into the vessel in the first step, and B is a length along the axial direction of the pipette tip from the distal end of the pipette tip to the second film when the pipette tip is inserted deepest into the pipette tip insertion part in the second step and the third step,
the pipette tip comprising:
a first part that includes the distal end of the pipette tip and has an outer diameter gradually increasing from a first distal end of the first part toward a first proximal end of the first part;
a second part that is arranged adjacent to the first part on the first proximal end, has an outer diameter being unchanged or gradually increasing from a second distal end of the second part toward a second proximal end of the second part, and has a smaller taper angle of an outer surface than a taper angle of an outer surface of the first part, wherein the second part is longer than the first part;
a third part that is arranged adjacent to the second part on the second proximal end, has an outer diameter gradually increasing from a third distal end of the third part toward a third proximal end of the third part, and has a larger taper angle of an outer surface than the taper angle of the outer surface of the first part; and
a fourth part that is arranged adjacent to the third part on the third proximal end, has an outer diameter being unchanged or gradually increasing from a fourth distal end of the fourth part toward a fourth proximal end of the fourth part, and has a smaller taper angle of an outer surface than the taper angle of the outer surface of the third part,
wherein there is no inflection part, in which a taper angle of an inner surface of the pipette tip decreases, between the first part and the second part.

13. A liquid delivery system comprising:
a vessel that has an opening closed with a first film and contains a liquid inside;
a channel chip that has a channel and a pipette tip insertion part, the pipette tip insertion part being connected to one end of the channel and having an opening closed with a second film; and
a pipette that has a pipette nozzle and a pipette tip attached to the pipette nozzle,
the liquid delivery system performing:
a first step of sucking the liquid contained in the vessel into the pipette tip in a state where the pipette tip is inserted through the first film into the vessel;
a second step of injecting the liquid retained in the pipette tip into the channel in a state where the pipette tip is inserted through the second film into the pipette tip insertion part of the channel chip; and
a third step of sucking the liquid in the channel into the pipette tip in a state where the pipette tip is inserted through the second film into the pipette tip insertion part of the channel chip, wherein
A>B is satisfied where A is a length along an axial direction of the pipette tip from a distal end of the pipette tip to the first film when the pipette tip is inserted deepest into the vessel in the first step, and B is a length along the axial direction of the pipette tip from the distal end of the pipette tip to the second film when the pipette tip is inserted deepest into the pipette tip insertion part in the second step and the third step, the pipette tip comprising:

a first part that includes the distal end of the pipette tip and has an outer diameter gradually increasing from a first distal end of the first part toward a first proximal end of the first part;

a second part that is arranged adjacent to the first part on the first proximal end, has an outer diameter being unchanged or gradually increasing from a second distal end of the second part toward a second proximal end of the second part, and has a smaller taper angle of an outer surface than a taper angle of an outer surface of the first part, wherein the second part is longer than the first part;

a third part that is arranged adjacent to the second part on the second proximal end, has an outer diameter gradually increasing from a third distal end of the third part toward a third proximal end of the third part, and has a larger taper angle of an outer surface than the taper angle of the outer surface of the first part; and a fourth part that is arranged adjacent to the third part on the third proximal end, has an outer diameter being unchanged or gradually increasing from a fourth distal end of the fourth part toward a fourth proximal end of the fourth part, and has a smaller taper angle of an outer surface than the taper angle of the outer surface of the third part, wherein there is no inflection part, in which a taper angle of an inner surface of the pipette tip decreases, between the first part and the second part.

* * * * *